(12) United States Patent
Silver et al.

(10) Patent No.: US 9,364,625 B2
(45) Date of Patent: Jun. 14, 2016

(54) WIRELESS VENTILATOR REPORTING

(75) Inventors: Annemarie Silver, Bedford, MA (US); Frederick J. Geheb, Danvers, MA (US); Gary L. Hochstetler, Groveland, MA (US); Vladimir Floroff, Lowell, MA (US); Gary A. Freeman, Newton Center, MA (US)

(73) Assignee: ZOLL MEDICAL CORPORATION, Chelmsford, MA (US)

( * ) Notice: Subject to any disclaimer, the term of this patent is extended or adjusted under 35 U.S.C. 154(b) by 291 days.

(21) Appl. No.: 13/081,217

(22) Filed: Apr. 6, 2011

(65) Prior Publication Data

US 2011/0284004 A1   Nov. 24, 2011

Related U.S. Application Data

(60) Provisional application No. 61/322,264, filed on Apr. 8, 2010.

(51) Int. Cl.
*F16K 31/02* (2006.01)
*A61M 16/00* (2006.01)
(Continued)

(52) U.S. Cl.
CPC ............ *A61M 16/0051* (2013.01); *A61B 5/087* (2013.01); *A61B 5/747* (2013.01); *A61M 16/0078* (2013.01); *A61M 16/0084* (2014.02); *A61N 1/3925* (2013.01); *A61B 5/002* (2013.01); *A61B 5/0022* (2013.01); *A61M 2016/0036* (2013.01); *A61M 2205/3553* (2013.01); *A61M 2205/3592* (2013.01); *A61M 2205/505* (2013.01); *A61M 2205/52* (2013.01);
(Continued)

(58) Field of Classification Search
CPC ............................ A61M 16/0051; A61B 5/747
USPC ............. 128/200.24, 202.13, 202.16, 202.22, 128/202.28, 202.29, 203.11, 204.18, 128/204.21, 205.13, 204.23; 601/41–44
See application file for complete search history.

(56) References Cited

U.S. PATENT DOCUMENTS 3,991,304 A  11/1976 Hillsman
6,269,267 B1  7/2001 Bardy et al.
(Continued)

FOREIGN PATENT DOCUMENTS

CN   1613097 A   5/2005
CN  101296730 A  10/2008
(Continued)

OTHER PUBLICATIONS

Authorized officer Trudy Hinterwimmer, International Search Report and Written Opinion in PCT/US2011/031347, mailed Sep. 30, 2011, 20 pages.
(Continued)

*Primary Examiner* — Kristen Matter
(74) *Attorney, Agent, or Firm* — The Webb Law Firm

(57) ABSTRACT

A medical ventilation monitoring system includes a patient ventilation unit defining an airflow path, the unit arranged so that when the unit is applied to a patient, the airflow path is in fluid communication with the patient's airway; an airflow sensor in the air flow path positioned to sense the presence of ventilation airflow to or from the patient; and a wireless transceiver arranged to receive data that is generated by a portable medical device, and to use the data to provide feedback to a rescuer regarding proper administration of ventilation.

41 Claims, 7 Drawing Sheets

(51) Int. Cl.
*A62B 7/00* (2006.01)
*A61B 5/087* (2006.01)
*A61B 5/00* (2006.01)
*A61N 1/39* (2006.01)

(52) U.S. Cl.
CPC .... *A61M2205/581* (2013.01); *A61M 2205/584* (2013.01); *A61M 2230/06* (2013.01); *A61M 2230/205* (2013.01); *A61M 2230/432* (2013.01); *A61N 1/3993* (2013.01)

(56) References Cited

U.S. PATENT DOCUMENTS

| | | | |
|---|---|---|---|
| 6,273,088 B1 | 8/2001 | Hillsman | |
| 6,980,112 B2 | 12/2005 | Nee | |
| 7,242,979 B1 | 7/2007 | Kelly et al. | |
| 2002/0133197 A1 | 9/2002 | Snyder et al. | |
| 2004/0162587 A1* | 8/2004 | Hampton et al. | 607/5 |
| 2005/0061315 A1 | 3/2005 | Lee et al. | |
| 2005/0085799 A1* | 4/2005 | Luria et al. | 606/1 |
| 2006/0129191 A1 | 6/2006 | Sullivan et al. | |
| 2007/0017521 A1* | 1/2007 | Ben et al. | 128/205.13 |
| 2007/0032830 A1 | 2/2007 | Bowers | |
| 2007/0162076 A1* | 7/2007 | Tan et al. | 607/5 |
| 2007/0169779 A1 | 7/2007 | Freeman | |
| 2007/0219588 A1 | 9/2007 | Freeman | |
| 2008/0027338 A1 | 1/2008 | Lu et al. | |
| 2008/0139948 A1* | 6/2008 | Stahmann et al. | 600/484 |
| 2008/0214948 A1 | 9/2008 | Myklebust et al. | |
| 2009/0163838 A1* | 6/2009 | Hecox et al. | 601/41 |
| 2009/0320836 A1* | 12/2009 | Baker, Jr. | 128/203.14 |
| 2010/0018530 A1 | 1/2010 | Schindhelm et al. | |
| 2010/0256539 A1* | 10/2010 | Strand et al. | 601/41 |
| 2011/0082510 A1 | 4/2011 | Sullivan | |
| 2011/0202100 A1* | 8/2011 | Tan et al. | 607/6 |
| 2012/0000464 A1* | 1/2012 | Gajic et al. | 128/202.22 |
| 2013/0009783 A1* | 1/2013 | Tran | 340/669 |
| 2013/0030173 A1* | 1/2013 | Wang et al. | 544/144 |

FOREIGN PATENT DOCUMENTS

| | | |
|---|---|---|
| CN | 101626797 A | 1/2010 |
| JP | 2007195977 A | 8/2007 |
| JP | 2007244879 A | 9/2007 |
| WO | 02/078775 | 10/2002 |

OTHER PUBLICATIONS

Authorized officer Trudy Hinterwimmer, Invitation to Pay Additional Fees in PCT/US2011/031347, mailed Jul. 11, 2011, 8 pages.
Aase et al., "CPR Artifact Removal from Human ECG Using Optimal Mutlichannel Filtering," IEEE Transactions on Biomedical Engineering 47(11):1440-1449 (2000).
Barash et al., "Novel Technology to Limit Chest Compression Interruption with Experienced Advanced Life Support Providers," American Heart Association Abstract P65, Circulation 2009, 120:S1455.
Li et al., "Identifying potentially shockable rhythms without interrupting cardiopulmonary resuscitation," Critical Care Medicine 36(1):198-203 (2008).
Lloyd et al., "Hands-On Defibrillation. An Analysis of Electrical Current Flow Through Rescuers in Direct Contact With Patients During Biphasic External Defibrillation," Journal of the American Heart Association Circulation 117:2510-2514 (2008).
Povoas et al., "Predicting the success of defibrillation by electrocardiographic analysis," Resuscitation 53:77-82 (2002).
Robertson et al., "Defibrillator Charging During On-Going Chest Compressions: A Multi-Center Study of In-Hospital Resuscitation," American Heart Association Abstract 2644, Circulation 2009, 120(18)2:S670.
Ruiz de Gauna et al., "A method to remove CPR artifacts from human ECG using only the recorded ECG," Resuscitation 76:271-278 (2008).
Silver et al., "A New Defibrillator Mode Reduces Chest Compression Interruptions for Lay Rescuers and BLS Providers," American Heart Association Abstract P173, Circulation 2009, 120:S1479.
Sullivan et al., "How Much Can Hands-off Time Be Reduced by Performing Rhythm Analysis During CPR?" American Heart Association Abstract P176, Circulation 2009, 120:S1479.
Yu et al., "The resuscitation blanket: A useful tool for "hands-on" defibrillation," Resuscitation 81:230-235 (2010).

* cited by examiner

WIRELESS VENTILATOR REPORTING

CROSS-REFERENCE TO RELATED APPLICATION

This application claims priority to U.S. Provisional Application Ser. No. 61/322,264, filed on Apr. 8, 2010, entitled "Wireless Ventilator Reporting," the entire contents of which is hereby incorporated by reference.

TECHNICAL FIELD

This document relates to systems and methods for regarding ventilation of a patient, such as a victim at the scene of an emergency.

BACKGROUND

Resuscitation treatments for patients suffering from cardiac arrest generally include clearing and opening the patient's airway, providing rescue breathing for the patient, and applying chest compressions to provide blood flow to the victim's heart, brain and other vital organs. If the patient has a shockable heart rhythm, resuscitation also may include defibrillation therapy. Such treatment may include basic life support (BLS), which involves initial assessment; airway maintenance; expired air ventilation (rescue breathing); and chest compression. When all these elements are combined, the term cardiopulmonary resuscitation (CPR) is used. Relatively untrained rescuers, such as laypeople, may provide BLS, while trained rescuers such as physicians or emergency medical technicians (EMTs) may provide advanced life support (ALS), which may additionally involve, among other things, cardiac monitoring, intravenous cannulation (IV), intraosseous (IO) access and intraosseous infusion, surgical cricothyrotomy, needle cricothyrotomy, and advanced medication administration through parental and enteral routes.

Ventilation in various instances may involve rescue breathing, or more commonly, bag or bag-valve-mask ventilation for ALS, which involves placing a mask in a seal over a patient's face and forcing air into the patient's lungs by repeatedly compressing and expanding a flexible device that is attached to the mask. Such ventilation may be performed in time-wise coordination with chest compressions and with defibrillation shocks delivered by a defibrillator, such as a portable defibrillator in the form of an automatic external defibrillator (AED) or other types of defibrillators. The chest compression can be automatically coordinated by the defibrillator, such as by the provision of an accelerometer positioned relative to the defibrillator electrodes on a patient's chest so that the accelerometer can be used to provide a rescuer with feedback if they are compressing too hard or too soft, and too fast or too slow, as compared to set standards and protocols.

SUMMARY

This document describes systems and techniques that may be used to monitor a caregiver's provision of ventilation to a medical patient. In one example, a ventilation monitor is placed in or on a ventilation assembly in the form of a ventilation bag and mask. The ventilation monitor may include a ventilation sensor for sensing a direction of ventilation (inhalation or exhalation of the patient) and may also include a sensor for sensing the volume of the patient's ventilation. The ventilation may include a transceiver for sending to an external unit such as a defibrillator or computing tablet a signal that indicates the occurrence of ventilation or respiration events (e.g., a signal for each exhalation, each inhalation, or both, or data otherwise representing a rate or volume of respiration in the patient). The external unit may then provide feedback to a rescuer, either directly or through the ventilation monitor, such as by providing a ventilation metronome (i.e., a sound that plays each time a rescuer is to provide ventilation) or by spoken feedback, such as feedback telling the provider of ventilation that they are providing too much or too little ventilation, or that they are going too fast or too slow.

The particular feedback may be directed to the particular patient and may be coordinated with other feedback given to a rescuer or rescuers. For example, the feedback may be coordinated with feedback for chest compressions so as to ensure that the provision of ventilation and of chest compressions stays synchronized. To prevent interference between the two feedback signals, the tones or other indications for chest compressions may be of one type (e.g., a beep or other hard sound that begins and ends crisply) and those for ventilation may be another (e.g., a whooshing or other soft noise that evokes the sound of breathing). Also, the feedback may be delivered wirelessly to headsets that are worn by each member of a rescue crew, where one headset delivers chest compression feedback and the other delivers ventilation feedback. The feedback may also be customized to the patient. For example, a rescuer may be asked a number of questions about the patient and the patient's condition, and the answers to the questions may affect the manner in which the rescuers are instructed to perform the rescue. Also, electronic medical record (EMR) data and dispatch information about the patient may also be accessed for similar reasons. For example, a victim who has suffered a traumatic brain injury will need tightly controlled ventilation, so that feedback prompting in such situations (e.g., when the criticality of proper ventilation or other operations on the victim) may be more overt to a rescuer (e.g., audible feedback may be louder, more insistent, or require rescuer confirmation) so as to assure that the rescuer focuses on appropriate ventilation technique.

In one implementation, a medical ventilation monitoring system is disclosed. The system comprises a patient ventilation unit defining an airflow path, the unit arranged so that when the unit is applied to a patient, the airflow path is in fluid communication with the patient's airway; an airflow sensor in the air flow path positioned to sense the presence of ventilation airflow to or from the patient; and a wireless transceiver arranged to receive data that is generated by a portable medical device, and to use the data to provide feedback to a rescuer regarding proper administration of ventilation. The ventilation unit can comprise a mask that seals to and fits over a lower portion of the patient's face, and can further include a flexible bag connected to provide ventilation air through the air flow path.

In some aspects, the airflow sensor comprises a differential pressure sensor. Also, the wireless transmitter can comprise a Bluetooth wireless transmitter. The system can also include a defibrillator having a wireless transceiver configured to communicate with the wireless transmitter so as to provide feedback to a rescuer in the vicinity of the wireless transmitter. The feedback can also comprise feedback that communicates to the rescuer an appropriate rate for providing ventilation to the patient. Moreover, the system can also include a portable computing device configured to receive inputs about a patient encounter from a medical caregiver, and programmed to generate a treatment regimen and to transmit data for implementing the treatment regimen.

In yet other aspects, the portable computing device is further programmed to transmit the data for implementing the treatment regimen to the patient ventilation unit, and can be further programmed to transmit a first portion of the data for implementing the treatment regimen to the patient ventilation unit, and a second portion of the data for implementing the treatment regimen to a portable defibrillator. Also, the portable computing device can be configured to receive input regarding a current condition of the patient, and to provide feedback to a rescuer based on one or more parameters that reflect the current condition of the patient. In addition, the rescuer input device can be programmed to receive input regarding a current condition of a patient by posing one or more questions to the rescuer about the patient, and to use answers to the one or more questions to determine an appropriate treatment regimen for the patient. The portable computing device can also be further programmed and arranged to upload information about the patient wirelessly to a central server system for sharing up the uploaded information to caregivers at a central medical facility. The system can further include a visual feedback mechanism for providing information to a rescuer regarding delivery of ventilation comprising a plurality of lights arranged to indicate, based on which lights of the plurality of lights are activated, whether excessive ventilation, too little ventilation, or an appropriate amount of ventilation is being provided to the victim.

In another implementation, a computer-implemented ventilation monitoring method for a patient is disclosed. The method comprises receiving at a portable computing device information about ventilation of a patient received from a transmitter connected to an airflow sensor in an artificial ventilation unit placed in or near the patient's airway; generating with the portable computing device a treatment approach for the patient; and providing feedback to a caregiver of the patient that incorporates the treatment approach. Providing feedback can comprise transmitting ventilation rate information to the artificial ventilation unit. The method can also comprise generating an audible or visual feedback signal on the artificial ventilation unit that indicates to a caregiver an appropriate ventilation rate for the patient. In addition, the method can include receiving at the portable computing device information about chest compressions performed on the patient from a sensor located near the patient's chest and providing feedback to a caregiver of the patient that incorporates the treatment approach. Moreover, the method can further comprise wirelessly uploading, from the portable computing device to a central server system, information about the patient collected during treatment of the patient by one or more caregivers.

In some aspects, the treatment approach is generated at least in part based on observations about a current condition of the patient provided by a caregiver to the portable computing device. Also, the treatment approach can be generated at least in part based on information from an electronic medical record for the patient. In addition, the portable computing device can comprise a general purpose tablet computer programmed to generate a treatment approach.

In yet another implementation, a medical ventilation monitoring device is disclosed that comprises a device housing having an inner wall that defines an airflow passage arranged to carry air provided to a person in need of assisted ventilation, an airflow sensor arranged to sense parameters of airflow in the airflow passage, and a wireless transceiver configured to provide information about the sensed parameters of airflow to an electronic device that is separate from the ventilation monitoring device, and to receive data from the remote electronic device that includes information for providing feedback for a user of the monitoring device regarding proper techniques for providing ventilation to the person. The device can further comprise an activation structure that, when selected, causes the ventilation monitoring device to attempt to establish a data connection with a wireless computing device. The activation structure can itself comprise a switch that is accessible from an exterior part of the ventilation monitoring device. Also, the activation structure can comprise a switch that is not accessible to a user of the device, and is activated by an action of the ventilation monitoring device being brought into proximity with a ventilation providing component. Moreover, the system can include a feedback mechanism for annunciating feedback instructions to a user of the device. The feedback mechanism can also comprise an LED light that blinks to indicate a proper ventilation rate for the person in need of assisted ventilation. The feedback mechanism can also comprise a speaker for creating an audible signal to indicate a proper ventilation rate for the person in need of assisted ventilation. In addition, the device can be further arranged to provide feedback regarding ventilation volume to be provided to the person via the speaker.

In certain aspects, the device housing is arranged to provide an airtight interface with components of an assisted ventilation assembly. The device housing can also be arranged to fit between an air bag and a face mask of an assisted ventilation assembly. The airflow sensor itself can comprise a differential pressure sensor.

In another implementation, a method for providing adaptive treatment to a person in need of emergency assistance is disclosed, and includes generating, with a portable computing device, an initial treatment protocol for providing care to the person in need of emergency assistance; receiving at the portable computing device information about a real-time current condition of the person in need of emergency assistance; generating a revised treatment protocol using the received information; and providing information for instructing one or more rescuers to provide emergency assistance to the person using the revised treatment protocol. Also, the received information can include information entered by a rescuer regarding a condition of the person observed by the rescuer. The method can also comprise sending data regarding the information for instructing the one or more rescuers to one or more medical devices that are separate from the portable computing unit. The portable computing unit can be integrated with a portable defibrillator, and the portable computing unit can comprise a touchscreen tablet computer.

In some aspects, the revised treatment protocol differs from any published protocol for treating a patient. Also, the initial and revised treatment protocols can define chest compression and ventilation rates for the person in need of emergency assistance. Moreover, the initial treatment protocol can follow a published protocol, and the revised treatment protocol can fail to follows the published protocol.

The details of one or more embodiments are set forth in the accompanying drawings and the description below. Other features and advantages will be apparent from the description and drawings, and from the claims.

DETAILED DESCRIPTION

This document describes mechanisms by which various devices can interact in a life-saving situation to improve the care that a victim (which should be understood to be a person in need of CPR, ventilation, or related care that is typically provided by an emergency medical technician or physician, but may also be provided by lay responders in certain situations) receives in such a situation. In particular, this document describes a system in which a patient ventilation sensor communicates with one or more other portable medical devices so that a ventilation rate, and perhaps a ventilation volume, may be analyzed, and a provider of care to the victim may be instructed in how best to ventilate the victim. The instructions may be coordinated with instructions for giving chest compressions to the victim and for defibrillating the victim. As one example, instructions regarding how fast, and when, to provide chest compressions and ventilation may be provided in a properly coordinated manner. Also, as a battery charges for a defibrillation pulse, such timing may be adjusted so that chest compressions and ventilation are finished as the defibrillator reaches a fully charged state, so that a defibrillation pulse may be delivered immediately upon the unit becoming charged. Also, the charging rate of the unit may be changed based on the location that rescuers are currently at in a protocol, so that the charging can occur at a rate that the device is ready at the proper point, and the device may be charged more slowly than it might otherwise be charged, thus conserving battery power in the device.

Figure 1:
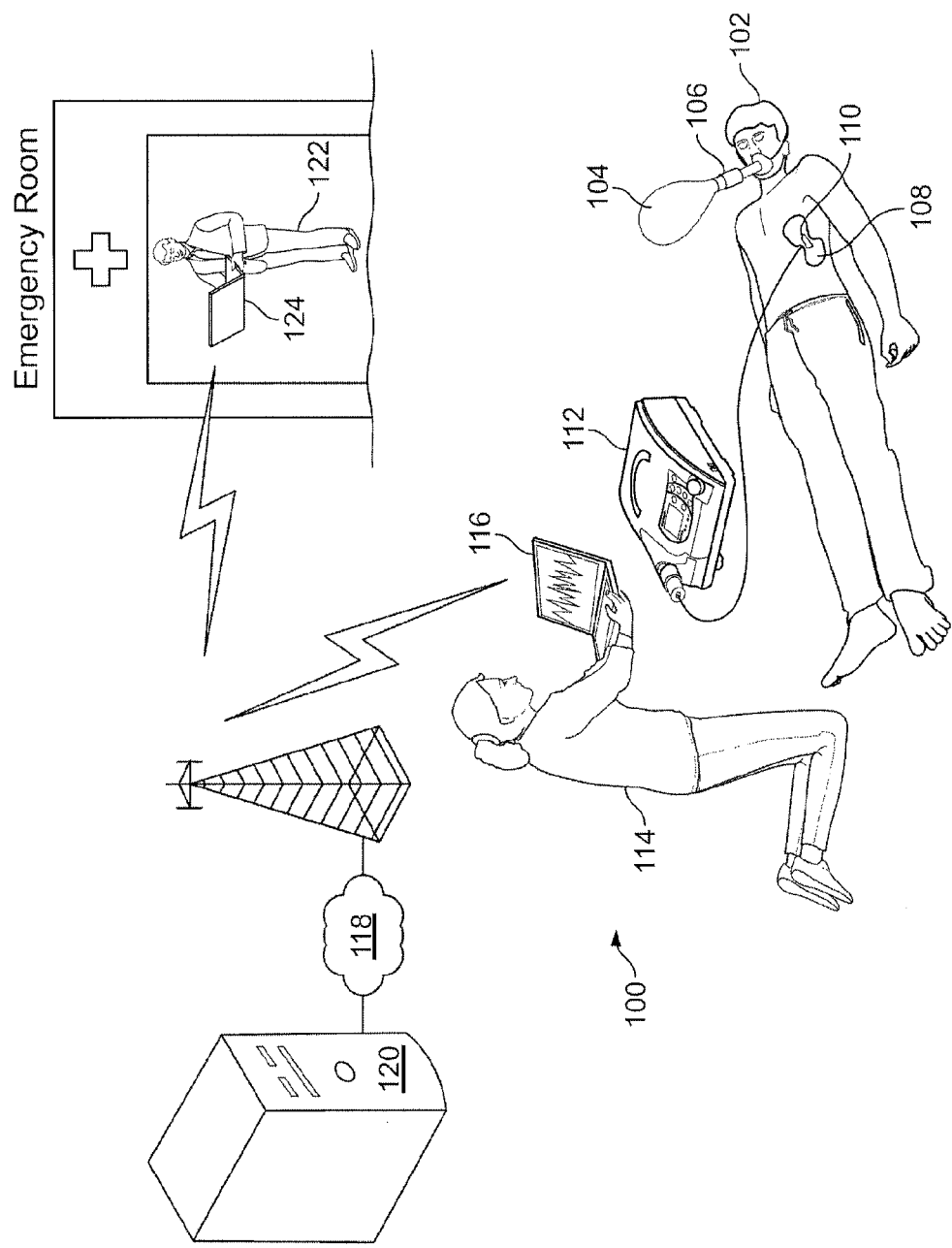
FIG. 1 shows a system for responding to an emergency medical condition.

FIG. 1 shows a system 100 for responding to an emergency medical condition. In general, system 100 includes various portable devices for monitoring on-site care given to a victim of an emergency situation, such as a victim 102 suffering from sudden cardiac arrest or a victim 102 at the scene of a traffic accident. The various devices may be provided by emergency medical technicians who arrive at the scene and who provide care for the victim 102, such as emergency medical technician 114. In this example, the emergency medical technician 114 has deployed several devices and is providing care to the victim 102. Although not shown, one or more other emergency medical technicians may be assisting and working in coordination with emergency medical technician 114 according to a defined protocol and training.

The emergency medical technician 114 in this example is interacting with a computing device in the form of a touch-screen tablet 116. The tablet 116 may include a graphical display by which to report information to the emergency medical technician 114, and may have an input mechanism such as a keyboard or a touchscreen by which the emergency medical technician 114 may enter data into the system 100. The tablet 116 may also include a wireless transceiver for communicating with a wireless network, such as a 3G or 4G chipset that permits long distance communication over cellular data networks, and further through the internet.

Separately, a portable defibrillator 112 is shown in a deployed state and is connected to the victim 102. In this example, electrodes 108 have been applied to the bare chest of the victim 102 and have been connected to the defibrillator 112, so that electrical shocking pulses may be provided to the electrodes in an effort to defibrillate the victim 102. The defibrillator 112 may take a variety of forms, such as the ZOLL MEDICAL R Series, E Series, or M Series defibrillators.

The assembly for the electrodes 108 includes a center portion at which an accelerometer assembly 110 is mounted. The accelerometer assembly 110 may include a housing inside which is mounted an accelerometer sensor configuration. The accelerometer assembly 110 may be positioned in a location where a rescuer is to place the palms of their hands when performing cardio pulmonary resuscitation (CPR) on the victim 102. As a result, the accelerometer assembly 110 may move with the victim's 102 chest and the rescuer's hands, and acceleration of such movement may be double-integrated to identify a vertical displacement of such motion.

The defibrillator 112 may, in response to receiving such information from the accelerometer assembly 112, provide feedback in a conventional and known manner to a rescuer, such as emergency medical technician 114. For example, the defibrillator 112 may generate a metronome to pace such a user in providing chest compressions. In addition, or alternatively, the defibrillator 112 may provide verbal instructions to the rescuer, such as by telling the rescuer that they are providing compressions too quickly or too slowly, or are pushing too hard or too soft, so as to encourage the rescuer to change their technique to bring it more in line with proper protocol—where the proper protocol may be a protocol generated by the system, but that is inconsistent with any published protocols.

The defibrillator 112 may communicate through a short range wireless data connection with the tablet 116, such as using BLUETOOTH technology. The defibrillator 112 can provide to the tablet 116 status information, such as information received through the electrode assembly 108, including ECG information for the victim 102. Also, the defibrillator 112 can send information about the performance of chest compressions, such as depth and rate information for the chest compressions. The tablet 116 may display such information (and also other information, such as information from the defibrillator regarding ETCO2 and SPO2) graphically for the emergency medical technician 114, and may also receive inputs from the emergency medical technician 114 to control the operation of the various mechanisms at an emergency site. For example, the emergency medical technician 114 may use the tablet 116 to change the manner in which the defibrillator 112 operates, such as by changing a charging voltage for the defibrillator 112.

Another electronic mechanism, in the form of a ventilation bag 104 is shown sealed around the mouth of the victim 102. The ventilation bag 104 may, for the most part, take a familiar form, and may include a flexible body structure that a rescuer may squeeze periodically to provide ventilation on the victim 102 when the victim 102 is not breathing sufficiently on his or her own.

Provided with the ventilation bag 104 is an airflow sensor 106. The airflow sensor 106 is located in a neck of the ventilation bag 104 near the mouthpiece or mask of the ventilation bag 104. The airflow sensor 106 may be configured to monitor the flow of air into and out of the patient's mouth, so as to identify a rate at which ventilation is occurring with the victim. In addition, in certain implementations, the airflow sensor 106 may be arranged to monitor a volume of airflow into and out of the victim 102.

In this example, the airflow sensor 106 is joined to a short-range wireless data transmitter or transceiver, such as a mechanism communicating via BLUETOOTH technology. As such, the airflow sensor 106 may communicate with the tablet 116 in a manner similar to the communication of the defibrillator 112 with the tablet 116. For example, the airflow sensor 106 may report information that enables the computation of a rate of ventilation, and in some circumstances a volume of ventilation, provided to the patient. The tablet 116, for example, may determine an appropriate provision of ventilation and compare it to the determine provision, and may provide feedback for a rescuer, either directly such as by showing the feedback on a screen of the tablet 116 or playing the feedback through an audio system of the tablet 116, or indirectly, by causing defibrillator 112 or airflow sensor 106 to provide such feedback. For example, defibrillator 112 or airflow sensor 106 may provide a metronome or verbal feedback telling a rescuer to squeeze the ventilation bag 104 harder or softer, or faster or slower. Also, the system 100 may provide the rescuer was an audible cue each time that the bag is to be squeezed and ventilation is to be provided to the victim 102.

Such feedback may occur in a variety of manners. For example, the feedback may be played on built-in loudspeakers mounted in any of tablet 116, defibrillator 112, or airflow sensor 106. Alternatively, or in addition, visual notifications may be provided on any combination of such units. Also, feedback may be provided to wireless headsets (or other form of personal device, such as a smartphone or similar device that each rescuer may use to obtain information and to enter data, and which may communicate wirelessly over a general network (e.g., WiFi or 3G/4G) or a small area network (e.g., BLUETOOTH) that are worn by each rescuer, and two channels of communication may be maintained, so that each rescuer receives instructions specific to their role, where one may have a role of operating the defibrillator 112, and the other may have the role of operating the ventilation bag 104. In this manner, the two rescuers may avoid being accidentally prompted, distracted, or confused by instructions that are not relevant to them.

A central server system 120 may communicate with the tablet 116 or other devices at the rescue scene over a wireless network and a network 118, which may include portions of the Internet (where data may be appropriately encrypted to protect privacy). The central server system 120 may be part of a larger system for a healthcare organization in which medical records are kept for various patients in the system. Information about the victim 102 may then be associated with an identification number or other identifier, and stored by the central server system 120 for later access. Where an identity of the victim 102 can be determined, the information may be stored with a pre-existing electronic medical record (EMR) for that victim 102. When the identity of the victim 102 cannot be determined, the information may be stored with a temporary identification number or identifier, which may be tied in the system to the particular rescue crew so that it may be conveniently located by other users of the system.

The information that is stored may be relevant information needed to determine the current status of the victim 102 and the care that has been provided to the victim 102 up to a certain point in time. For example, vital signs of the victim 102 may be constantly updated at the central server system 120 as additional information is received from the tablet 116. Also, ECG data for the victim 102 may be uploaded to the central server system 120. Moreover, information about drugs provided to the victim may be stored. In addition, information from a dispatch center may also be stored on a central server system and accessed by various users such as rescuers. For example, a time at which a call came in may be stored, and rescuers (either manually or automatically through their portable computing devices) can use that time to determine a protocol for treating the patient (e.g., ventilation or chest compression needs may change depending on how long the victim has been in need of treatment).

Other users may then access the data in the central server system 120. For example, as shown here, an emergency room physician 122 is operating his or her own tablet 124 that communicates wirelessly, such as over a cellular data network. The physician 122 may have been notified that victim 102 will be arriving at the emergency room, and, in preparation, may be getting up-to-speed regarding the condition of the victim 102, and determining a best course of action to take as soon as the victim 102 arrives at the emergency room. As such, the physician 122 may review the data from central server system 120. In addition, the physician 122 may communicate by text, verbally, or in other manners with emergency medical technician 114. In doing so, the physician 122 may ask questions of the emergency medical technician 114 so that the physician 122 is better prepared when the victim 102 arrives at the emergency room. The physician 122 may also provide input to the emergency medical technician 114, such as by describing care that the emergency medical technician 114 should provide to the victim 102, such as in an ambulance on the way to the emergency room, so that emergency room personnel do not have to spend time performing such actions. Also, physicians could see aspects of a currently-operating protocol on the system, and could act to override the protocol, with or without the rescuers needing to know that such a change in the protocol has been made (e.g., their devices will just start instructing them according to the parameters for the manually revised protocol).

Where the published protocol is organized in a flowchart form, the flowchart may be displayed to a rescuer or a physician, and such user may drag portions of the flowchart to reorder the protocol. Alternatively, the user could tap a block in the flowchart in order to have parameters for that block displayed, so that the user can change such parameters (e.g., ventilation volume or time between ventilations). Data describing such an edited protocol may then be saved with other information about an incident so that later users may review it, and a user may save reordered protocols so that they can be employed more easily and quickly in the future.

In this manner, the system 100 permits various portable electronic devices to communicate with each other so as to coordinate care that is provided to a victim 102. Each such device may sense information about the care provided to the victim 102, and/or may provide instructions or may store data about such care. As a result, the system 100 may provide improved care for the victim 102 by better integrating and coordinating each form of the care that the victim 102 receives. The victim 102 made thus receive improved care and an improved chance of obtaining a positive outcome from an event.

In certain instances, a condition of a victim that is used to generate a protocol for treatment of the victim may be based on on-site observations made by a rescuer, by information in an EMR for the victim, or both. For example, a determination from an EMR that a victim is taking a particular drug may result in a change in protocol for ventilation rate. Likewise, an observation by a rescuer that the victim has suffered a head injury on site may also affect the protocol for ventilation rate. The two factors may also be considered together to determine yet a more refined ventilation rate for which a rescuer will be instructed to provide to the victim.

Thus, in operation, a two-person rescue team may arrive at a scene. One member of the team may set up and attach a defibrillator, and do the same with a ventilation bag assembly. The other member may begin an examination of the victim and enter information obtained from the examination into a portable computing device such as a general tablet computer (e.g., an iPad or netbook). In some situations, the second rescuer may be able to verbally interview the victim, at least initially, so as to determine whether the victim is lucid, what drugs the victim may be taking, and the like. The second rescuer could also make visual observations (e.g., types of trauma to the victim) and record those in the computing device. Moreover, one of the rescuers may obtain vital sign information for the victim, and such information may be entered manually into the computing device or automatically, such as through wireless links from a blood pressure cuff, or other relevant medical device.

The computing device, using all of the entered information, may then generate a protocol for treating the victim. Such a generating may occur by selecting from among a plurality of available protocols by plugging the observations into a protocol selector. The generation may also be more dynamic, and may depends on a series of heuristics that use the observations as inputs, and generate a protocol (which may be made up of one or more sub-protocols) as an output. Moreover, a lookup table may be consulted, where the table may define correlations between particular observed patient conditions or physical parameters, and a particular feature of a treatment protocol.

The computing device may also submit the observation information over a network such as the internet, and a protocol may be generated by a central computer server system and then automatically downloaded to, and implemented by, the portable computing device. Such an approach may have the benefit of being able to easily update and modify protocol-generation rules.

The computing device may then receive information about the performance by the rescuers, such as from wired or wireless transmitters on a defibrillator, an assisted ventilation unit, or other medical device (e.g., blood pressure reader). The computing device may provide feedback or coaching when the performance falls out of line with a defined protocol, or may provide feedback to maintain the performance in line with the protocol. Also, the computing device may update the protocol as care is being provided to the victim. For example, the rate of required ventilation or chest compressions may change as a function of time. Also, if one of the rescuers attaches an oxygen source to a ventilation assembly (as sensed, e.g., by a switch where the connection occurs, by a manual rescuer input to the system, or by sensors in the assisted ventilation system), the rate of required ventilation may change. Other changes in the patient condition, such as changes in measured levels of ETCO2 or SpO2, can lead to the computing device generating a revised protocol and providing feedback to the rescuers so that they adapt to the revised protocol (sometimes without consciously knowing that the protocol has been revised).

Figure 2:
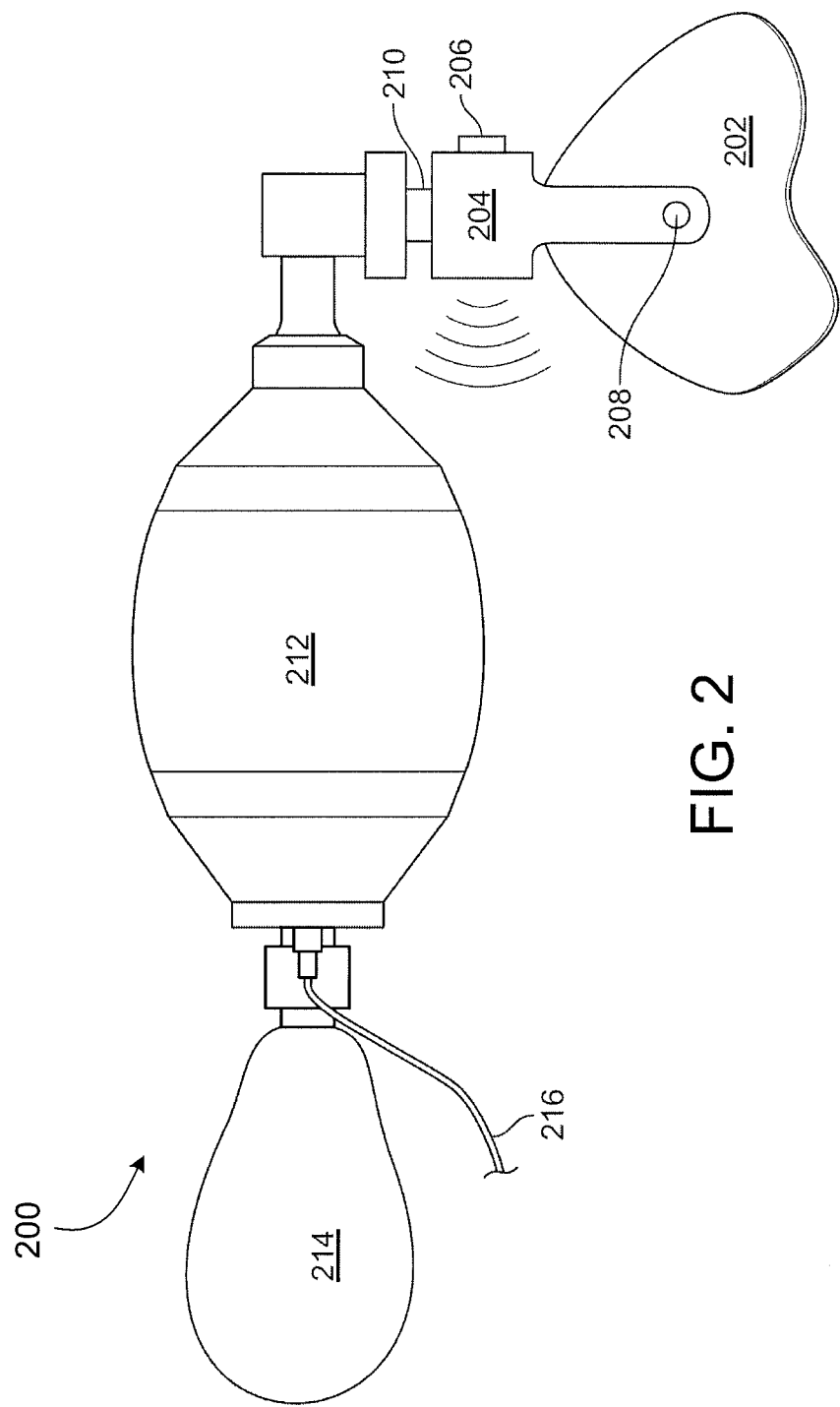
FIG. 2 shows an example of an airflow sensor.

FIG. 2 shows an example of an airflow sensor 204 used with a ventilation bag assembly 200, which may be used to ventilate a patient or victim of an accident. In this example, the airflow sensor 204 is mounted as an integral part of the ventilation bag assembly 200. The assembly 200 includes a face mask 202 which is formed from a flexible material that is configured to produce a tight seal around the periphery of a victim's mouth so that air provided by the assembly 200 may be forced into the victim's airway, and thus the victim may be properly ventilated.

The force for ventilating the patient is provided by compression of a ventilation bag body 212, which itself may be made of a flexible material that is sized and shaped so that the rescuer may place his or her hands around the body 212 and squeeze to force ventilation air into a victim. A reservoir attached to the body 212 may serve as an area for mixing of gases to be introduced, in a familiar manner. An oxygen supply line 216 is also provided and connected to the body 212, so that supplemental oxygen may be conveniently provided to a victim by way of the ventilation bag assembly 200.

A neck 210 extends from the body 212 and forms a right angle for purposes of permitting the assembly 200 to be held in a comfortable position relative to a victim's face when the mask 202 is sealed to the face. The neck 212 is a tube having a round cross-section that defines an airflow path in its interior portion, so that air may flow out of the body 212. Through the neck 210, and into the mask 202. Attached between the neck 210 and the mask 202 is the airflow sensor 204. The airflow sensor 204 may itself define an interior passage that is matched to an exterior diameter of an extension of the neck 210 and an extension of the mask 202. As a result, the airflow sensor 204 may be friction fit over such extensions, allowing the airflow sensor 204 to be added conveniently to a system that is not designed initially to have an airflow sensor, such as airflow sensor 204.

The airflow sensor 204 may operate in various known manners to detect and measure the presence of airflow in or out of a victim, and in certain implementations, to measure a volume of airflow in or out of the victim. For example, the airflow sensor 204 may include a differential pressure sensor that is attached to a venturi mechanism in an airflow path inside sensor 204. A differential pressure sensor may also be provided in coordination with a beam that substantially bisects an air flow path inside sensor 204. Taps from the differential pressure sensor may extend from discrete sides of the beam, so that the presence and volume of airflow may be determined by the difference in pressure measured between the taps. The beam may be positioned and shaped so as to provide more accurate readings, in known manners.

The sensor 204 may include an activation button 206 that, when pressed, causes the sensor 204 to activate and to begin attempting to communicate with other medical devices in its vicinity. The sensor 204, for example, may communicate using BLUETOOTH technology and may establish a connection with another device through standard BLUETOOTH handshaking mechanisms. Once the wireless connection is made, the device 204 may determine how frequently to send updates to another medical device, and may begin sending such updates. In certain implementations, the sensor 204 may also receive input from such other devices, such as input for providing a rescuer with instruction in the performance of rescue operations.

Although shown externally in the figure for manual activation, the button 206 may be mounted internally to sensor 204, such that it is activated as soon as neck 210 is inserted into sensor 204. The button 206 may instead be represented by a magnetic switch that is automatically activated when the sensor 204 is assembled with the neck 210 or the mask 202. The sensor 204 may also be activated in other relevant manners such as by a mercury switch, motion detector, or other appropriate mechanism.

An LED light 208 is shown connected to the sensor 204 and may be used to provide feedback to a user of the sensor 204. For example, the LED light 208 may blink each time ventilation is to be provided to a victim, so as to provide visual orientation for a rescuer. In this example, the LED light 208 is shown at the end of an elongated flexible strip, so as to position the LED light 208 at a location that is more likely to be seen by a rescuer, and less likely to be blocked visually by the body 212 of ventilation bag assembly 200. The LED light 208 can also be mounted directly in the body of sensor 204 in appropriate circumstances.

In other implementations, multiple modes of feedback may be provided (e.g., both rate and volume). In such a situation, a first LED, which may backlight a letter "R" for rate, and another may backlight a letter "V" for volume, and/or a pair of LEDs may be located on opposed sides of the letter, with lighting of an LED behind the letter indicating that the rate or volume being applied by the rescuer, respectively, is correct. The LEDs to the side of the letter may be lit alternatively, depending on whether the rescuer is being prompted to increase or decrease their rate or volume of ventilation.

The assembly 200 thus enables the performance of ventilation on a victim to be monitored and feedback to be provided to a rescuer. Such feedback may be provided from a computing device that takes into account various parameters of the victim's medical history and/or current medical condition, and coordinates the activities of the various medical devices that are treating the victim at one time.

Other sensors, not shown here, may also be used with a monitoring and feedback system. For example, airway gas detectors may be used, including to determine a level of oxygen that is being provided to a patient through a mask. In addition, differential absorption characteristics of CO2 in red and infrared (IR) wavelengths may also be measured. Also, trans-thoracic impedance may be measured in order to determine, for example, when problems with an intubation have occurred (e.g., the tube becomes dislodged from bouncing on stairs or in an ambulance). Checks for intubation tube status can also be linked to the air flow sensor, so that the checks are begun when ventilation of the victim begins. The various coordinated sensors may also be used, in certain instances, to move a procedure outside of a standard protocol, or to follow a protocol that has been designed to be more flexible and responsive to patient needs than are typical protocols that depend on the limited capabilities of one or two caregivers.

Also, sensors other than airflow sensors may be used to determine a ventilation rate. For example, a strain sensor may be provided on the bag of a ventilation assembly, and may be used to determine how frequently the bag is being squeezed, and by extension the rate of assisted ventilation being provided to a victim.

Figure 3:
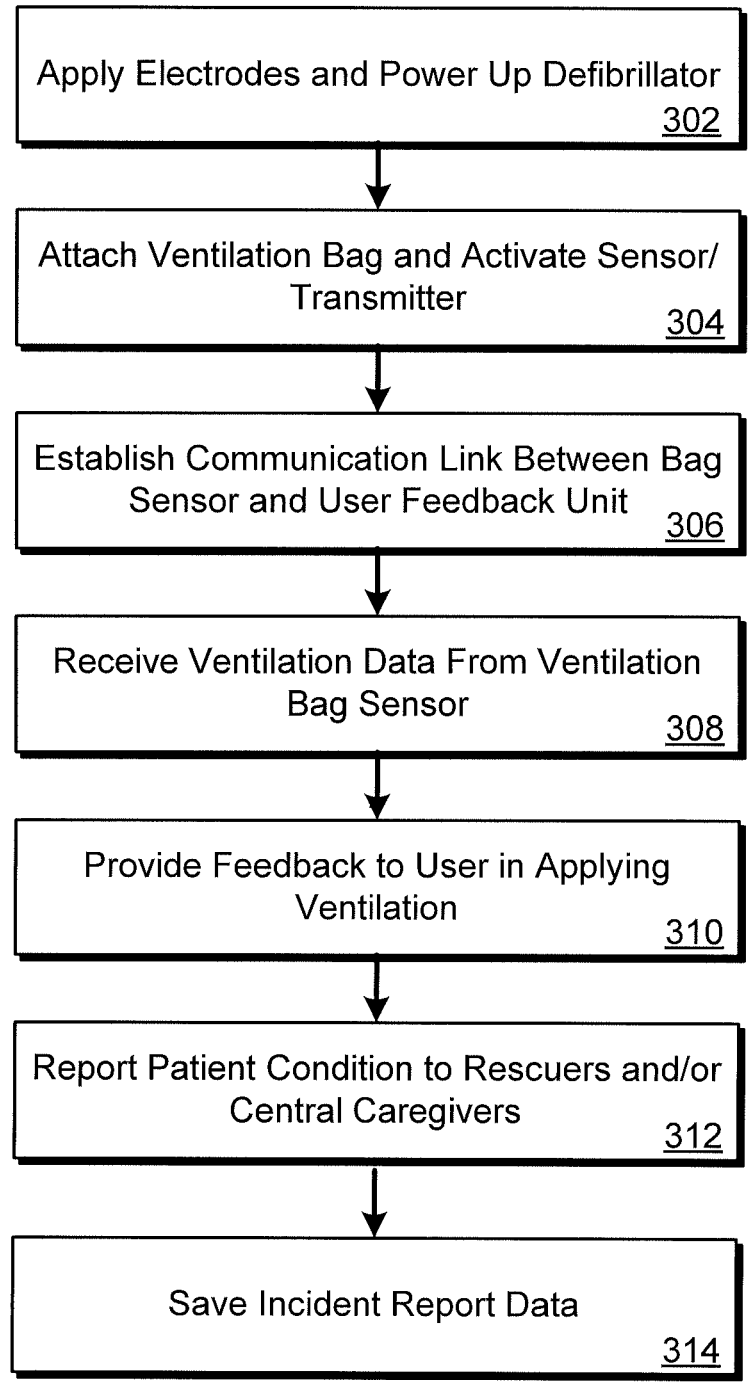
FIG. 3 is a flowchart of a process for providing feedback to a caregiver who is operating a ventilation bag or similar structure.

FIG. 3A is a flowchart of a process for providing feedback to a caregiver who is operating a ventilation bag or similar structure. In general, the process involves deploying various medical devices at the scene of an emergency and causing the devices to coordinate their operations so as to improve the care that is given to a victim at the scene.

The process begins a box 302, where electrodes for a defibrillator are applied to a victim and the defibrillator is powered up. Such action may occur soon after rescuers, who may be lay rescuers using an AED or emergency medical technicians using an advanced defibrillator, arrive on a scene and recognize that a victim is in need of defibrillation.

At box 304, a ventilation bag is attached to the victim and an airflow sensor associated with the bag is activated. In one example, a second emergency medical technician may be assigned this task and may recognize that the victim's airway is patent and is not in need of incubation at the moment, and may deploy the ventilation bag to begin providing forced ventilation to the victim.

At box 306, a communication link is established between the bag airflow sensor and a feedback unit, which may be in the form of a tablet, like tablet 116 in FIG. 1, or a defibrillator like defibrillator 112 in FIG. 1. The communication may occur automatically upon activating the two communicating components, such as by instigating an automatic BLUETOOTH or WiFi connection in a familiar manner.

At box 308, ventilation data is received from the ventilation bag airflow sensor. The ventilation data may simply include time stamped indicators of the start or end of inhalation and/or exhalation for the victim. The data may also include information about the length of inhalation or exhalation, and the volume of air moved by the victim or for the victim. Such information may be passed from the airflow sensor to a computing component such as tablet 116. The data may then be compared against a protocol for providing ventilation, and determinations may be made with respect to whether the ventilation is being properly or improperly applied relative to that protocol. Also, coordination of the ventilation with other actions being taken on the victim (e.g., chest compressions) may also be performed via a device such as tablet 116.

Upon the device making such determinations, it may provide feedback to the rescuer in applying ventilation, as shown at box 310. For example, the tablet 116 may provide visual or audible feedback to guide a rescuer regarding when and with how much force to squeeze a ventilation bag. The tablet 116 may also communicate data to another device, such as a defibrillator or back to the airflow sensor, and that receiving device may provide the feedback to the caregiver. In addition, information may be provided to a headset or other personal interface worn by the particular rescuer, which may enable feedback provided to one rescuer to be separated from feedback provided to the other rescuer, so that the rescuers are less likely to become confused with the feedback. In addition, other communications may occur through such headsets, such as communications between cooperating caregivers, and communications from a dispatch center or from a central physician such as an emergency room physician who is tracking the progress of the team of the EMTs, or providing input to such a team.

The feedback provided may follow a set protocol that does not differ from victim to victim, or may be customized for the particular victim. For example, the rate and volume of ventilation to provide a victim may depend on how long the victim has been suffering from a current condition. Thus, a rescuer may try to ascertain how long the victim has been down, or a time stamp from the time at which an emergency was called in may be used as a proxy. Also, various states o the victim may be relevant to the rate and volume of ventilation to be provided to the victim, including:

pediatric vs. adult patient condition (e.g. traumatic brain injury vs. cardiac arrest)

Characteristics of the ECG may also suggest different ventilation requirements. For example, patients with ventricular fibrillation may have lower ventilation requirements than patients with asystole or PEA.

Etiology of disease-cardiac arrest due to drowning vs. presumed myocardial infarction Duration of patient downtime for cardiac arrest Presence/absence of (effective) bystander CPR (compressions and/or ventilations) prior to arrival of EMS ETCO2—there are recommendations to titrate ventilation rate to achieve a particular end tidal CO2 value.

SpO2—adjust ventilation rate to achieve optimal peripheral oxygen saturation

At box 312, the system reports the victim's condition to rescuers and may also report the condition of the victim to central caregivers, such as physicians or other staff in an emergency room where the victim will be taken. Such reporting may include providing ECG readout information, vital signs, and other relevant information needed by the immediate (e.g., EMT's) or secondary (e.g., ER Physicians) caregivers.

At box 314, incident report data is saved, such as by sending the data from one or more of the portable medical devices at a scene to a central electronic medical record system. The data may be gathered initially at one device such as tablet 116, and may then be forwarded to the central system. The incident report data may include information regarding drugs and other treatments provided to the patient, and other information that may be relevant to downstream caregivers, such as emergency room physicians.

In this manner, and using this example process, information relating to various aspects of care given to a victim at the scene of an accident may be collected, and treatment of the patient may be coordinated, including by coordinating the provision of chest compressions, defibrillation shocks, and ventilation to the patient.

Figure 4:
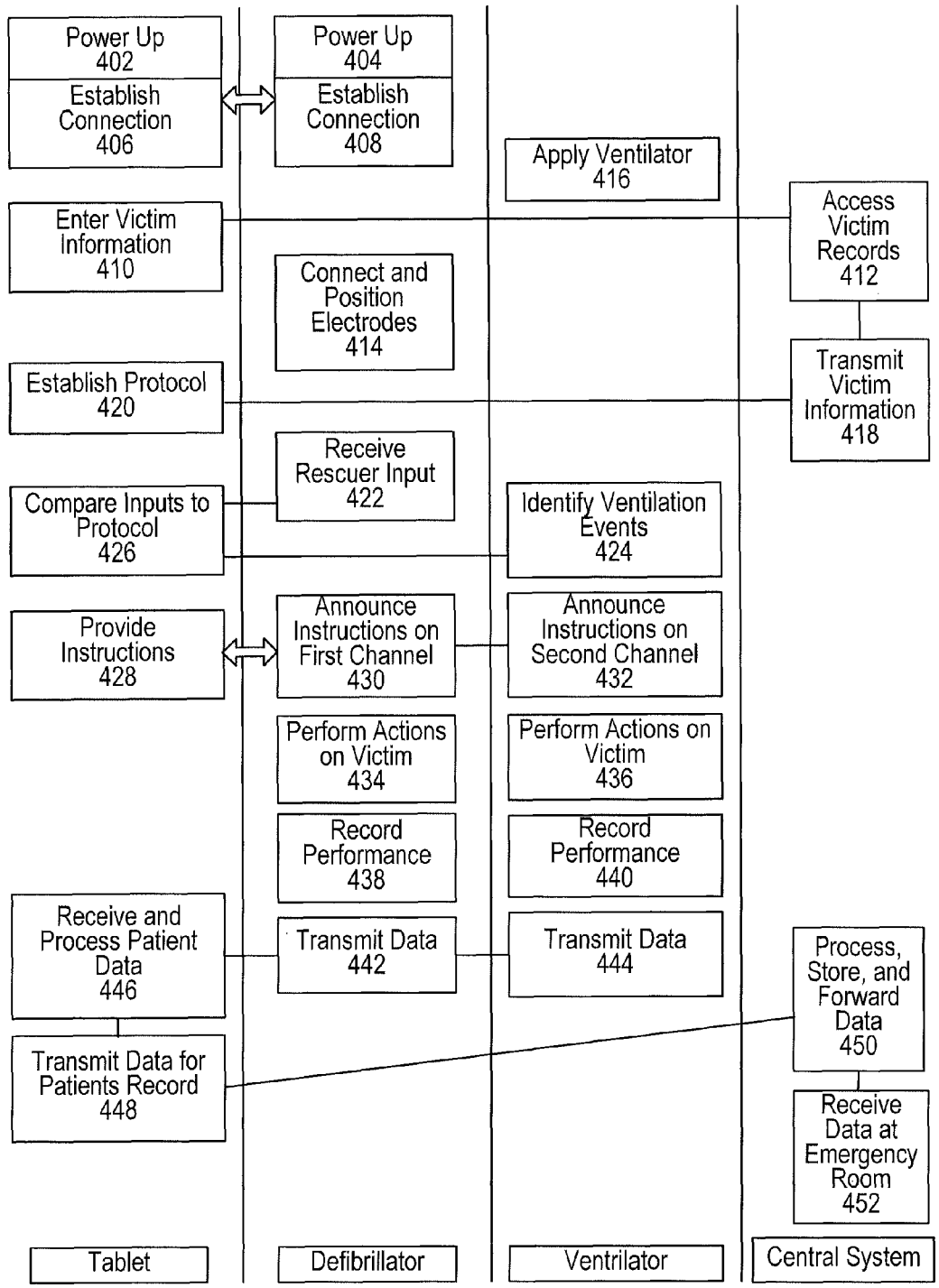
FIG. 4 is a swim lane diagram of a process by which various parameters can be used to provide feedback to one or more medical rescuers.

FIG. 4A is a swim lane diagram of a process by which various parameters can be used to provide feedback to one or more medical rescuers. In general, the process is similar to that shown in FIG. 3A, though particular example structures are shown in this figure as performing certain steps in the process. The particular steps that are carried out by each structure or device can be changed as is appropriate, and other steps may be added, steps may be rearranged or modified, or steps may be removed from the process.

The process begins at boxes 402 and 404, where a tablet and defibrillator are powered up at the site of an emergency. Such powering may simply involve deploying them from emergency vehicles and activating power switches on each such device. At boxes 406 and 408, a wireless communication connection is established between the tablet and the defibrillator for the transfer of data between the two devices while care is being provided to a victim at the emergency scene.

At box 410, victim information is entered into the tablet (though at least some of the information may also have been previously entered by a dispatcher, and that information may auto-populate on the device). Such information may include a name or alphanumeric ID number of the victim, as a mechanism for retrieving electronic medical record information about the victim. Such information may also include information about the current condition of the victim. For example, a caregiver may record whether the victim has suffered head trauma, whether the victim is bleeding, has broken bones, approximately age and gender of the victim, and other information that may be relative to the care to be given to the victim. Such information may be entered on a touchscreen display, including by selecting input values from a menuing system (including a system that performs a question-and-answer interview session with a rescuer), or could also be provided by a spoken input to the tablet.

Where an identifier for a victim, such as a name of the victim is provided, the tablet may attempt to access records in a central system, as shown by box 412. Where the tablet has provided appropriate credentials, such as identifier and password of an emergency medical technician, the central system may transmit medical record information about the victim, at box 418, back to the tablet. Upon receiving additional information about the victim, the tablet may establish a protocol for treatment of the victim, and may begin carrying out the protocol by instructing rescuers at the scene. For example, the condition of the victim, the victim's age, the victim's medical history, and the victim's size, may all be relevant to the manner in which chest compressions, defibrillation shocks, and ventilation are provided to the victim. The protocol established by the tablet may take into account each relevant factor in developing a plan of treatment.

While the system is obtaining data and developing a plan, a caregiver at the site may be connecting and positioning electrodes on the victim's chest (box 414), and the same caregiver or another caregiver may be applying a ventilator (box 416) on the victim.

The caregivers may then begin executing the protocol, such as by applying chest compressions and ventilation to the victim. At boxes 422 and 424, the defibrillator provides received rescue data to the tablet, such as by transmitting information regarding the victim's ECG and also the manner in which chest compressions have been applied to the victim, and the ventilator or ventilation sensor may provide information about ventilator events. Such information may include, for example, the frequency with which ventilation is being applied, and also the volume of ventilation air being provided.

At box 426, the tablet compares the received inputs to the appropriate protocol, which may be a static protocol or may be a dynamic protocol that changes as treatment of the victim continues. Where the inputs do not match the protocol so that corrective action by the caregivers is required, the tablet may provide instructions (box 428) to the caregivers. For example, the tablet may transmit information to the defibrillator, and the defibrillator may be caused to announce instructions to a provider of chess compressions, such as having a speaker on the defibrillator state those instructions (box 430). The tablet may also send data to the ventilator, causing the ventilator to announce instructions to another caregiver (box 432), either visually or audibly.

At boxes 434 and 436, respectively, the caregiver providing chest compressions and operating the defibrillator may follow the received instructions, and a caregiver operating the ventilating device may follow the other appropriate instructions. At boxes 438 and 440, respectively, the defibrillator and the ventilator may record the performance of the particular caregiver in response to the instructions. Such performance data may be stored and transmitted back to the tablet at boxes 442 and 444. The data may indicate whether the relevant caregivers have altered their actions sufficiently to place their activities back within the protocol ranges. Also, the protocol may change over time, such as by calling for a certain period of chess compressions followed by the provision of electric shock to the patient for defibrillation. Thus, the tablet, at box 428 may change the instructions that it provides so as to match the changes in the protocol.

At box 446, the tablet receives and processes the patient data. The process may then loop back to box 428 and until treatment of the victim is completed. Changes may be made to the protocol as treatment continues also, such as by recognizing that the patient has been without a normal heart rhythm for particular time, and adjusting the timing and sequencing of care given to the victim based on such a determination.

At box 448, data is transmitted for the patient's record to the central system. Such data may be provided consistently throughout provision of care, such as by providing ECG and vital signs data that may be reviewed in real time by a central emergency room physician who accesses the central system. The data may also be provided when the care is complete, such as may be recognized by the powering down of the tablet, defibrillator, or ventilator, so that the medical devices may be returned to an ambulance or other vehicle in which the patient is transported to an emergency room. Also, the tablet may invoke additional dialogue with one of the caregivers on such a trip, so as to complete the patient record before the caregivers move to another project.

At box 450, the central system processes, stores, and forwards, relevant data regarding the victim. For example, the treatment information, such as drugs that may have been given to the patient through intravenous tubes, may be recorded and added to the victim's medical record. In addition, a billing system may be notified, and appropriate fees may be applied to a victim's account in such a system. Moreover, a snapshot of relevant data from the treatment may be provided in advance to an emergency room team at a hospital where the patient has been taken. Then, at box 452, the relevant data is received at the emergency room, so that the emergency room team can review it when providing further treatment for the patient.

Figure 5:
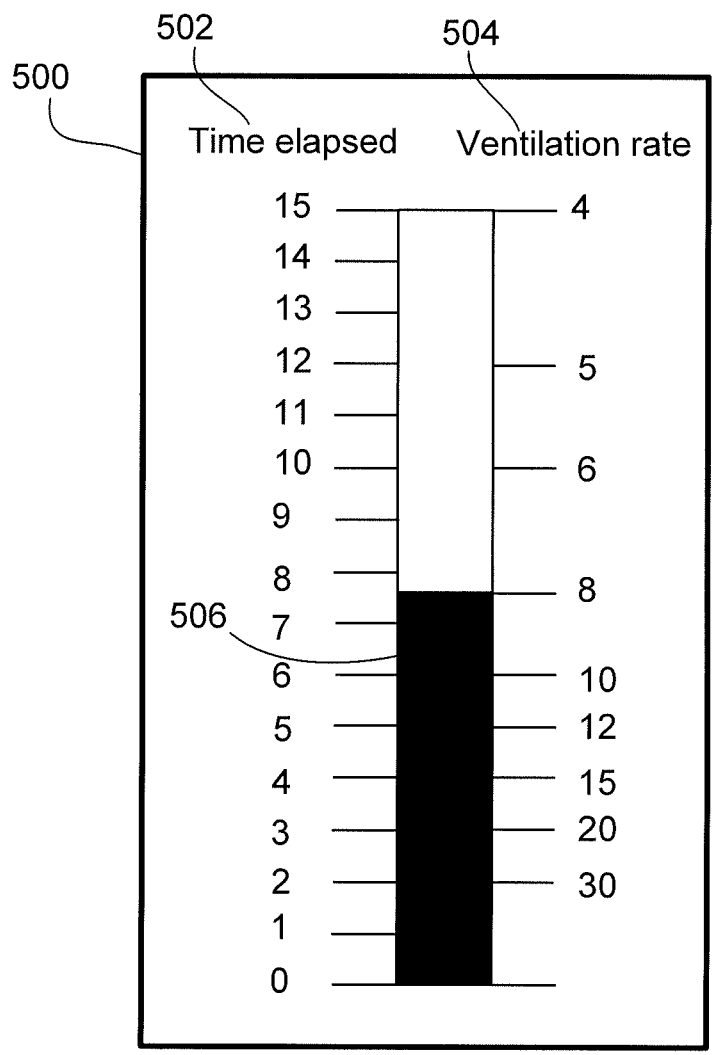
FIGS. 5 and 6 show an example of a visual feedback provided to a caregiver.

FIG. 5 shows exemplary information, e.g., a ventilation timer 500, displayed on a display device to a rescuer during the administration of ventilation to a patient. The ventilation timer 500 provides information to the rescuer to help the rescuer control the rate of ventilation provided to the patient. The ventilation timer 500 can include a bar 506 (or other shape) that that fills as time elapses between breaths. The bar 506 can include scaling information (e.g., tick marks on the graph) that provide information about the elapsed time 502 and/or ventilation rate 504. The elapsed time 502 provides an indication of the amount of time that has passed since the last ventilation event and the respiration rate 504 provides the number of breaths per minute (e.g., 5 seconds between breaths=12 breaths/minute).

The information displayed on the ventilation timer 500 is based on ventilation related data received from a device that detects when a ventilation has been delivered (e.g., a flow meter, capnography, thoracic impedance). The ventilation related information is used by a computer to provide an input indicating when to re-start the timer such that the elapsed time can be determined.

In some examples, the information presented on the ventilation timer 500 can be color coded or otherwise supplemented by a visual indicator of ranges that indicate adequate ventilation versus sub-optimal ventilation. In one example, the color of the bar 506 in the ventilation timer can change based on the adequacy of the ventilation. For example, the bar could be colored green when proper ventilation is being provided and yellow or red when the ventilation falls outside the desired range of respiration rates. Additionally, in some examples, an indication of whether the user should increase or decrease the rate of respiration could be provided. Additionally, in some examples, an indication of the optimal elapsed time/ventilation rate could be provided such as by overlaying a line or other indicator at the desired level so the rescuer can attempt to have the bar 506 match the displayed optimal timing indicator.

In some additional examples, the information presented in the ventilation timer 500 can be color coded or otherwise supplemented by other visual indicator based on the nature of the underlying condition being treated, e.g. respiratory distress vs cardiac arrest vs TBI. Additionally, the range that is indicated as an optimal or an acceptable respiration rate can change based on information from one or more physiologic monitoring sensors and estimate from those sensor(s) of the underlying status of the patient's cardiopulmonary status. Such physiologic monitoring can be based, for example on information about $EtCO_2$ (e.g., the partial pressure or maximal concentration of carbon dioxide, $CO_2$ at the end of an exhaled breath, which is expressed as a percentage of $CO_2$ or mmHg) and/or information about oxygen saturation from a pulse oximeter, a medical device that indirectly monitors the oxygen saturation of a patient's blood. Such physiologic monitoring can also include information from a tissue $CO_2$ sensor that can be used to calculate the blood oxygen concentration, for example, based on the ventilation/perfusion ratio (or V/Q ratio) which provides a measurement used to assess the efficiency and adequacy of the matching of the amount air reaching the alevoli to the amount of blood reaching the alveoli (sometimes reported as the VQ mismatch which is used to express when the ventilation and the perfusion of a gas exchanging unit are not matched).

Figure 6:
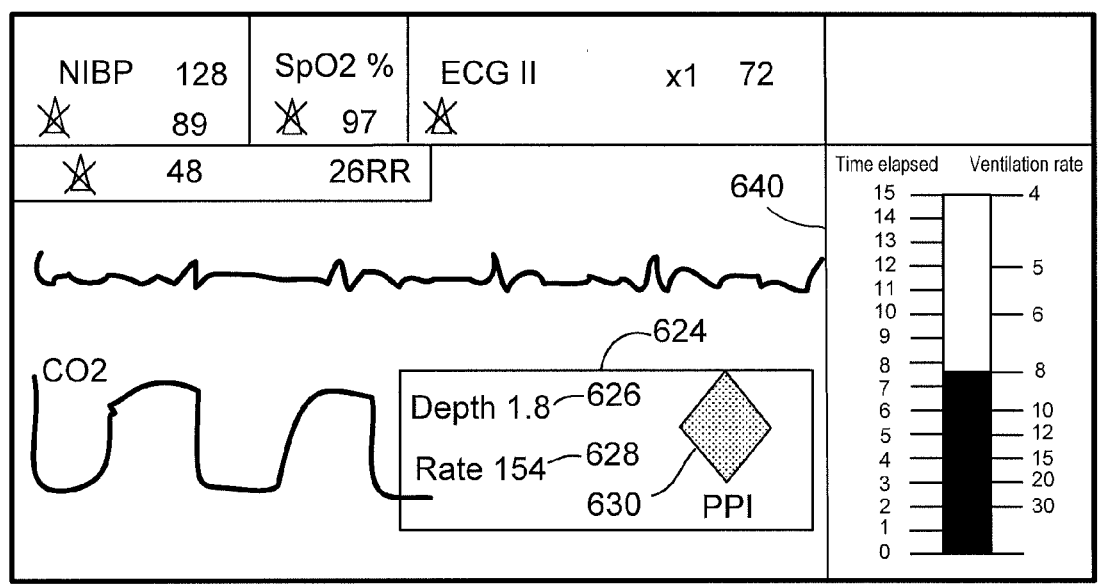

FIG. 6 shows exemplary information displayed during the administration of ventilation and CPR compressions to a patient. The system automatically switches the information presented based on whether chest compressions are detected and whether appropriate ventilation is detected. For example, CO2 or depth of chest compressions may be displayed (e.g., a CO2 waveform 620 is displayed in FIG. 8B) during CPR administration and upon detection of the cessation of chest compressions the waveform can be switched to display and SpO2 or pulse waveform (not shown).

A portion 640 of the display can include ventilation information such as a ventilation timer (e.g., as described above in relation to FIG. 5) providing information about respiratory rate associated with the elapsed time between ventilations.

Another portion 624 of the display can include information about the CPR such as depth 626, rate 628 and perfusion performance indicator (PPI) 630. 520. The PPI 630 is a shape (e.g., a diamond) with the amount of fill in the shape differing to provide feedback about both the rate and depth of the compressions. When CPR is being performed adequately, for example, at a rate of about 100 compressions/minute (CPM) with the depth of each compression greater than 1.5 inches, the entire indicator will be filled. As the rate and/or depth decreases below acceptable limits, the amount of fill lessens. The PPI 520 provides a visual indication of the quality of the CPR such that the rescuer can aim to keep the PPI 520 completely filled.

Figure 7:
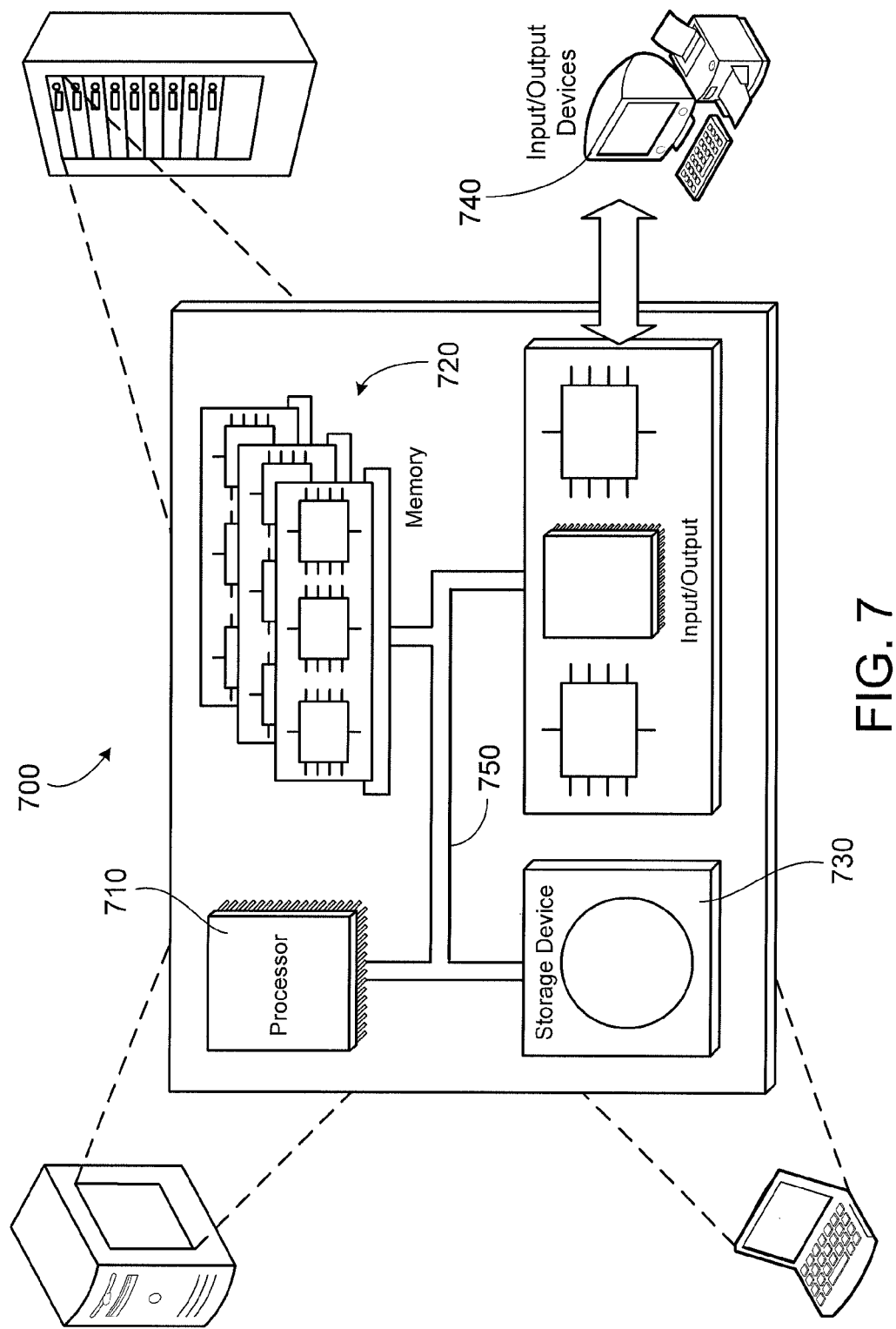
FIG. 7 is a schematic diagram of a general computing system that can be employed to operate a medical device in manners like those discussed here.

FIG. 7 is a schematic diagram of a computer system 700. The system 700 can be used for the operations described in association with any of the computer-implement methods described previously, according to one implementation. The system 700 is intended to include various forms of digital computers, such as laptops, desktops, workstations, personal digital assistants, servers, blade servers, mainframes, and other appropriate computers. The system 700 can also include mobile devices, such as personal digital assistants, cellular telephones, smartphones, and other similar computing devices. Additionally the system can include portable storage media, such as, Universal Serial Bus (USB) flash drives. For example, the USB flash drives may store operating systems and other applications. The USB flash drives can include input/output components, such as a wireless transmitter or USB connector that may be inserted into a USB port of another computing device.

The system 700 includes a processor 710, a memory 720, a storage device 730, and an input/output device 740. Each of the components 710, 720, 730, and 740 are interconnected using a system bus 750. The processor 710 is capable of processing instructions for execution within the system 700. The processor may be designed using any of a number of architectures. For example, the processor 710 may be a CISC (Complex Instruction Set Computers) processor, a RISC (Reduced Instruction Set Computer) processor, or a MISC (Minimal Instruction Set Computer) processor.

In one implementation, the processor 710 is a single-threaded processor. In another implementation, the processor 710 is a multi-threaded processor. The processor 710 is capable of processing instructions stored in the memory 720 or on the storage device 730 to display graphical information for a user interface on the input/output device 740.

The memory 720 stores information within the system 700. In one implementation, the memory 720 is a computer-readable medium. In one implementation, the memory 720 is a volatile memory unit. In another implementation, the memory 720 is a non-volatile memory unit.

The storage device 730 is capable of providing mass storage for the system 700. In one implementation, the storage device 730 is a computer-readable medium. In various different implementations, the storage device 730 may be a floppy disk device, a hard disk device, an optical disk device, or a tape device.

The input/output device 740 provides input/output operations for the system 700. In one implementation, the input/output device 740 includes a keyboard and/or pointing device. In another implementation, the input/output device 740 includes a display unit for displaying graphical user interfaces.

The features described can be implemented in digital electronic circuitry, or in computer hardware, firmware, software, or in combinations of them. The apparatus can be implemented in a computer program product tangibly embodied in an information carrier, e.g., in a machine-readable storage device for execution by a programmable processor; and method steps can be performed by a programmable processor executing a program of instructions to perform functions of the described implementations by operating on input data and generating output. The described features can be implemented advantageously in one or more computer programs that are executable on a programmable system including at least one programmable processor coupled to receive data and instructions from, and to transmit data and instructions to, a data storage system, at least one input device, and at least one output device. A computer program is a set of instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

Suitable processors for the execution of a program of instructions include, by way of example, both general and special purpose microprocessors, and the sole processor or one of multiple processors of any kind of computer. Generally, a processor will receive instructions and data from a read-only memory or a random access memory or both. The essential elements of a computer are a processor for executing instructions and one or more memories for storing instructions and data. Generally, a computer will also include, or be operatively coupled to communicate with, one or more mass storage devices for storing data files; such devices include magnetic disks, such as internal hard disks and removable disks; magneto-optical disks; and optical disks. Storage devices suitable for tangibly embodying computer program instructions and data include all forms of non-volatile memory, including by way of example semiconductor memory devices, such as EPROM, EEPROM, and flash memory devices; magnetic disks such as internal hard disks and removable disks; magneto-optical disks; and CD-ROM and DVD-ROM disks. The processor and the memory can be supplemented by, or incorporated in, ASICs (application-specific integrated circuits).

To provide for interaction with a user, the features can be implemented on a computer having a display device such as a CRT (cathode ray tube) or LCD (liquid crystal display) monitor for displaying information to the user and a keyboard and a pointing device such as a mouse or a trackball by which the user can provide input to the computer.

The features can be implemented in a computer system that includes a back-end component, such as a data server, or that includes a middleware component, such as an application server or an Internet server, or that includes a front-end component, such as a client computer having a graphical user interface or an Internet browser, or any combination of them. The components of the system can be connected by any form or medium of digital data communication such as a communication network. Examples of communication networks include a local area network ("LAN"), a wide area network ("WAN"), peer-to-peer networks (having ad-hoc or static members), grid computing infrastructures, and the Internet.

The computer system can include clients and servers. A client and server are generally remote from each other and typically interact through a network, such as the described one. The relationship of client and server arises by virtue of computer programs running on the respective computers and having a client-server relationship to each other.

A number of embodiments have been described. Nevertheless, it will be understood that various modifications may be made without departing from the spirit and scope of the invention. Accordingly, other embodiments are within the scope of the following claims.

What is claimed is:

1. A medical ventilation monitoring system, comprising:
a patient ventilation unit defining an airflow path, the unit arranged so that when the unit is applied to a patient, the airflow path is in fluid communication with the patient's airway, the patient ventilation unit including:
an airflow sensor positioned to sense the presence of ventilation airflow to or from the patient, and
a wireless transceiver; and
a portable computing device separate from the ventilation unit and arranged to communicate with the wireless transceiver, the portable computing device configured to:
provide an initial treatment protocol for providing care to the patient, the initial treatment protocol being executed includes applying ventilation at an initial ventilation rate and at an initial ventilation volume,
receive data regarding a current condition of the patient from the wireless transceiver and information from a remote medical system, and
determine an updated treatment protocol, the updated treatment protocol being executed includes applying ventilation at an updated ventilation volume different from the initial ventilation volume, or at an updated ventilation rate different from the initial ventilation rate, the updated treatment protocol being based at least in part on information from the airflow sensor and the information from the remote medical system.

2. The system of claim 1, wherein the portable computing device is further configured to provide information for implementing the updated treatment protocol.

3. The system of claim 2, wherein the portable computing device is configured to provide information for implementing the updated treatment protocol by transmitting data to the patient ventilation unit.

4. The system of claim 2, wherein the portable computing device is configured to provide information for implementing the updated treatment protocol to a rescuer.

5. The system of claim 1, wherein the patient ventilation unit comprises a mask that seals to and fits over a lower portion of the patient's face.

6. The system of claim 5, wherein the patient ventilation unit further comprises a flexible bag connected to provide ventilation air through the air flow path.

7. The system of claim 1, wherein the airflow sensor comprises a differential pressure sensor.

8. The system of claim 1, wherein the wireless transmitter comprises a Bluetooth wireless transmitter.

9. The system of claim 1, further comprising a defibrillator having a wireless transceiver configured to communicate with the wireless transmitter so as to provide feedback to a rescuer in the vicinity of the wireless transmitter.

10. The system of claim 9, wherein the feedback comprises feedback that communicates to the rescuer an appropriate rate for providing ventilation to the patient.

11. The system of claim 9, wherein the portable computing device is further configured to receive inputs about a patient encounter from a medical caregiver, and programmed to generate a treatment regimen and to transmit data for implementing the treatment regimen.

12. The system of claim 11, wherein the portable computing device is further programmed to transmit the data for implementing the treatment regimen to the patient ventilation unit.

13. The system of claim 11, wherein the portable computing device is further programmed to transmit a first portion of the data for implementing the treatment regimen to the patient ventilation unit, and a second portion of the data for implementing the treatment regimen to the defibrillator.

14. The system of claim 1, wherein the portable computing device is configured to receive input regarding a current condition of the patient, and to provide feedback to a rescuer based on one or more parameters that reflect the current condition of the patient.

15. The system of claim 14, wherein the portable computing device is programmed to receive input regarding a current condition of a patient by posing one or more questions to the rescuer about the patient, and to use answers to the one or more questions to determine an appropriate treatment regimen for the patient.

16. The system of claim 1, wherein the portable computing device is further programmed and arranged to upload information about the patient wirelessly to a central server system for sharing the uploaded information to caregivers at a central medical facility.

17. The system of claim 1, further comprising a visual feedback mechanism for providing information to a rescuer regarding delivery of ventilation comprising a plurality of lights arranged to indicate, based on which lights of the plurality of lights are activated, whether excessive ventilation, too little ventilation, or an appropriate amount of ventilation is being provided to the victim.

18. The system of claim 1, further comprising a visual feedback mechanism for providing information to a rescuer regarding delivery of ventilation comprising a ventilation timer providing information about respiratory rate.

19. The system of claim 1, further comprising a visual feedback mechanism for providing information to a rescuer regarding delivery of ventilation comprising a ventilation timer providing information about elapsed time between ventilation events.

20. A ventilation monitoring method for a patient, the method comprising:
applying ventilation to a patient at an initial ventilation rate and at an initial ventilation volume;
receiving at a portable computing device information about the ventilation of the patient received from a transmitter connected to an airflow sensor in an artificial ventilation unit placed in or near an airway of the patient;
receiving, at the portable computing device, information from a remote medical system;
generating with the portable computing device an updated treatment approach for the patient, the updated treatment approach being executed includes applying ventilation at an updated ventilation volume different from the initial ventilation volume, or at an updated ventilation rate different from the initial ventilation rate, the updated ventilation rate and the updated ventilation volume being based at least in part on the information about ventilation of the patient and the information from the remote medical system; and
providing feedback to a caregiver of the patient that incorporates the updated treatment approach.

21. The method of claim 20, wherein providing feedback comprises transmitting ventilation rate information to the artificial ventilation unit.

22. The method of claim 21, further comprising generating an audible or visual feedback signal on the artificial ventilation unit that indicates to a caregiver an appropriate ventilation rate for the patient.

23. The method of claim 21, further comprising displaying a visual feedback mechanism that provides information about respiratory rate.

24. The method of claim 21, further comprising displaying a visual feedback mechanism that provides information about elapsed time between ventilation events.

25. The method of claim 20, further comprising receiving at the portable computing device information about chest compressions performed on the patient from a sensor located near the patient's chest and providing feedback to a caregiver of the patient that incorporates the treatment approach.

26. The method of claim 20, further comprising wirelessly uploading, from the portable computing device to a central server system, information about the patient collected during treatment of the patient by one or more caregivers.

27. The method of claim 20, wherein the treatment approach is generated at least in part based on observations about a current condition of the patient provided by a caregiver to the portable computing device.

28. The method of claim 27, wherein the treatment approach is generated at least in part based on information from an electronic medical record for the patient.

29. The method of claim 28, wherein the portable computing device comprises a general purpose tablet computer programmed to generate a treatment approach.

30. A medical ventilation monitoring device, comprising:
a device housing having an inner wall that defines an airflow passage arranged to carry air provided to a person in need of assisted ventilation;
an airflow sensor arranged to sense parameters of airflow in the airflow passage; and
a wireless transceiver configured to:
provide information about the sensed parameters of airflow to a portable computing device that is separate from the ventilation monitoring device, and
receive, from the portable computing device, data that includes information for providing feedback for a user of the ventilation monitoring device regarding proper techniques for providing ventilation to the person,
wherein the proper techniques being executed includes applying ventilation at an updated rate of ventilation for application to the patient different from an initial rate of ventilation, or an updated ventilation volume for application to the patient that is different from an initial ventilation volume, and
at least one of the updated rate of ventilation and the updated ventilation volume is based at least in part on data received by the portable computing device from a remote medical system and on the parameters of airflow in the airflow passage determined by the airflow sensor.

31. The device of claim 30, further comprising an activation structure that, when selected, causes the ventilation monitoring device to attempt to establish a data connection with a wireless computing device.

32. The device of claim 31, wherein the activation structure comprises a switch that is accessible from an exterior part of the ventilation monitoring device.

33. The device of claim 31, wherein the activation structure comprises a switch that is not accessible to a user of the device, and is activated by an action of the ventilation monitoring device being brought into proximity with a ventilation providing component.

34. The device of claim 30, further comprising a feedback mechanism for annuciating feedback instructions to a user of the device.

35. The device of claim 34, wherein the feedback mechanism comprises an LED light that blinks to indicate a proper ventilation rate for the person in need of assisted ventilation.

36. The device of claim 34, wherein the feedback mechanism comprises a speaker for creating an audible signal to indicate a proper ventilation rate for the person in need of assisted ventilation.

37. The device of claim 34, wherein the feedback mechanism comprises a ventilation timer.

38. The device of claim 34, wherein the device is further arranged to provide feedback regarding ventilation volute to be provided to the person via a speaker.

39. The device of claim 30, wherein the device housing is arranged to provide an airtight interface with components of an assisted ventilation assembly.

40. The device of claim 39, wherein the device housing is arranged to fit between an air bag and a face mask of an assisted ventilation assembly.

41. The device of claim 30, wherein the airflow sensor comprises a differential pressure sensor.

* * * * *